| United States Patent [19] | [11] Patent Number: 4,489,207 |
| Becker et al. | [45] Date of Patent: Dec. 18, 1984 |

[54] PREPARATION OF 2-(HYDROXYPHENOXY)-CARBOXYLATES

[75] Inventors: Rainer Becker, Bad Durkheim; Heinz-Günter Oeser, Dirmstein; Rolf-Dieter Acker, Leimen, all of Fed. Rep. of Germany

[73] Assignee: BASF Aktiengesellschaft, Ludwigshafen, Fed. Rep. of Germany

[21] Appl. No.: 450,380

[22] Filed: Dec. 16, 1982

[30] Foreign Application Priority Data

Dec. 18, 1981 [DE] Fed. Rep. of Germany ....... 3150233

[51] Int. Cl.$^3$ ............................................. C07C 69/76
[52] U.S. Cl. ...................................... 560/61; 564/254; 260/465 D
[58] Field of Search .......................... 560/61; 564/254; 260/465 D

[56] References Cited

U.S. PATENT DOCUMENTS 4,153,803  5/1979  Thiele et al. ........................... 560/61
4,227,009  10/1980  Koch et al. ............................ 560/61

FOREIGN PATENT DOCUMENTS 1591063  6/1981  United Kingdom .

OTHER PUBLICATIONS

J. Org. Chem., vol. 39, No. 2, 1974, Newman et al., "Studies on the Monoalkylation of Hydroquinone."
J. Amer. Chem. Soc., 72 (1950), 1413, C. M. Moser, "The Reaction of Hydroquinone with Ethyl Chloroacetate."

*Primary Examiner*—Paul J. Killos
*Attorney, Agent, or Firm*—Oblon, Fisher, Spivak, McClelland & Maier

[57] ABSTRACT

2-(Hydroxyphenoxy)-carboxylates are prepared by a process wherein a dihydroxybenzene (A) is reacted with a 2-halo-fatty acid ester (B) of an alcohol, phenol or oxime of no more than 10 carbon atoms, in a molar ratio of A:B ≧ 1.5, in the presence of calcium hydroxide in dimethylsulfoxide, at from 0° to 100° C.

6 Claims, No Drawings

PREPARATION OF 2-(HYDROXYPHENOXY)-CARBOXYLATES

The present invention relates to a process for the preparation of 2-(hydroxyphenoxy)-carboxylates, some of which are known. These compounds are suitable intermediates for the synthesis of biological, in particular herbicidal, active ingredients.

It has been disclosed that selective monoalkylation of dihydroxybenzenes is difficult because both hydroxyl groups tend to react with the alkylating agent. Thus, Newman and Cella, J. Org. Chem. 39 (1974), 214 et seq., describe, inter alia, the alkylation of hydroquinone, in the form of its disodium salt, with a 2-bromocarboxylate in certain water-soluble organic solvents. However, it has been found that this method cannot be used generally. The process disclosed in German Laid-Open Application DOS No. 2,824,828, in which hydroquinone is reacted with a 2-halocarboxylate in an alcoholic solution in the presence of sodium alcoholate, can be employed only in the case of esters with low molecular weight ester groups, and is unsuccessful even in the case of butyl esters; furthermore, the optical activity of the ester used as a starting material is not retained in the product obtainable by this process. Finally, Moser, J. Amer. Chem. Soc. 72 (1950), 1413 et seq., discloses that hydroquinone may be reacted with ethyl chloroacetate in the presence of boron trifluoride, but monosubstitution and disubstitution of the hydroquinone occur side by side in this method.

We have found that the above difficulties can be overcome and that 2-(hydroxyphenoxy)-carboxylates of the general formula

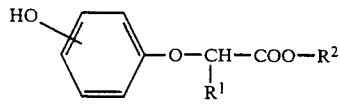

where $R^1$ is hydrogen or a low molecular weight alkyl group, preferably methyl or ethyl, and $R^2$ is a saturated or unsaturated hydrocarbon radical of no more than 10 carbon atoms which is unsubstituted or substituted by phenoxy, cyano, halogen or trialkylsilyl, or is a radical of the formula

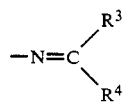

where $R^3$ and $R^4$ are each identical or different hydrocarbon radicals which are of no more than 9 carbon atoms together, may also be bonded to one another and are unsubstituted or substituted, can be obtained in an advantageous manner if a compound of the formula

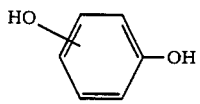

is reacted with a 2-halo-fatty acid ester of the formula

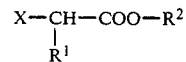

where $R^1$ and $R^2$ have the above meanings and X is chlorine or bromine, in the presence of calcium hydroxide in dimethylsulfoxide, at from 0° to +100° C., the molar ratio of the starting materials II:III at the beginning of the reaction being not less than 1.5:1.

The starting material of the formula II is hydroquinone, resorcinol or pyrocatechol, the two first-mentioned compounds being preferred. The starting materials of the formula III are known, or may be obtained by a conventional process, for example by the esterification of an alcohol, phenol or oxime of the formula HO-$R^2$ with a chloride or anhydride of chloroacetic or bromoacetic acid or higher homologs of these acids, for example especially 2-chloropropionic, 2-bromopropionic, 2-chlorobutyric or 2-bromobutyric acid. In this formula, $R^2$ has the above meanings, and may be, in particular, a straight-chain or branched alkyl, alkenyl, alkynyl, cycloalkyl, aryl or aralkyl radical of no more than 10, preferably of no more than 8, carbon atoms, or a radical of an open-chain or cyclic ketoxime. $R^2$ may be substituted; with regard to the activity of the end products, for the preparation of which the substances obtainable according to the invention are intermediates, suitable substituents are, in particular, phenoxy, cyano, halogen, in particular bromine and chlorine, and trialkylsilyl.

Specific examples of starting materials of the formula III are methyl bromoacetate, ethyl chloroacetate, the methyl, ethyl, n-propyl, 2-phenoxyethyl, 3-phenoxypropyl, n-butyl, isobutyl, t-butyl, n-pentyl, n-octyl, 2-ethylhexyl, n-decyl, allyl, propargyl, 2-cyanoethyl, 1-cyanopropyl, 3-chloroallyl, 2,3-dichloroallyl, 2-bromoallyl and phenyl esters of 2-chloro- and 2-bromopropionic acid, ethyl 2-bromobutyrate, 1-cyanocylohexyl 2-bromobutyrate, ethyl 2-bromovalerate, methyl 2-bromocaproate, 2-bromopropionylacetoxime and bromoacetylcyclohexanone oxime.

Compounds of the formula III in which $R^1$ is alkyl possess an asymmetrically substituted carbon atom, and may therefore occur as a racemate or in an optically active form. A particular advantage of the novel process is that, when an optically active starting material of the formula III is used, the optical activity is retained in the product of the formula I.

The process according to the invention is carried out in solution in an organic solvent. Of the many organic solvents which are suitable in principle, one in particular is able completely to satisfy all requirements in respect of selectivity of monosubstitution, yield and wide range of use, i.e. dimethylsulfoxide.

The molar ratio in which the starting materials are employed is important for the success of the novel process. Thus, not less than 1.5, preferably about 2, moles of the compound of the formula II should be employed per mole of starting material of the formula III. This ratio may also be exceeded, but as a rule this has no advantages. About 0.5 mole of calcium hydroxide is employed in general per mole of the compound of the formula II. Deviation from this ratio has, as a rule, no advantages, and usually it is not advisable to use less than 0.4 mole or more than 1.0 mole of calcium hydroxide per mole of the compound of the formula II.

The novel process is carried out at from 0° to 100° C., particularly advantageously from 0° to 60° C. To a certain extent, the most favorable reaction temperature is dependent on the choice of reactants. Thus, among the compounds of the formula III, the 2-bromo-fatty acid esters react at lower temperatures than the corresponding chlorine compounds. For the first-mentioned compounds, therefore, about 0°-20° C. has proved particularly suitable; the lower limit is governed by the risk of the reaction medium solidifying, while the danger of appreciable disubstitution of the compounds of the formula II becomes greater, the greater the amount by which the above range is exceeded. 2-Bromo-fatty acid esters are most safely employed at about 10° C. In contrast, 2-chloro-fatty acid esters of the formula III are preferably employed at a higher temperature, ie. in general at about 25°-90° C., particularly advantageously at about 50° C. Where either a particular 2-bromo-fatty acid ester or the corresponding chlorine compound may be chosen as a starting material for carrying out the novel process, in general the bromine compound is preferably employed because it usually gives a higher yield of the desired product.

The novel process is advantageously carried out as follows: the starting material of the formula II is dissolved in dimethylsulfoxide, the finely divided calcium hydroxide is dispersed in this solution and the starting material of the formula III is added slowly to the mixture, while maintaining the desired reaction temperature. Advantageously, the solvent should contain only a small amount, for example less than 1%, of water. The amount of solvent used can be varied within a wide range, for example from 0.2 to 1 liter per mole of the compound II being suitable. As a rule, the reaction is complete in the course of a few hours. The product is isolated by a conventional method, for example by introducing the mixture into acidified water and separating off the precipitated products. If the products are liquid, as they are in a large number of cases, they can be purified, for example, by distillation, and where they are solid, they can be purified, for example, by distillation or crystallization.

Using the novel process, the majority of the compounds of the formula I are obtained in yields of from 60 to 80% of theory and more, especially when 2-bromo-fatty acid esters are employed as starting materials of the formula III. If the corresponding chlorine compounds are used as starting materials, the yields in many cases are lower. However, the selectivity in respect of monosubstitution of the compounds of the formula II is excellent in both cases.

The 2-(hydroxyphenoxy)-carboxylates prepared by the process according to the invention are useful intermediates for the synthesis of biological, in particular herbicidal, active ingredients, as described in, for example, the following publications: German Laid-Open Application DOS No. 2,223,894, German Laid-Open Application DOS No. 2,433,067, German Laid-Open Application DOS No. 2,546,251, German Laid-Open Application DOS No. 2,812,571, German Laid-Open Application DOS No. 2,820,032, German Laid-Open Application DOS No. 2,914,300, German Laid-Open Application DOS No. 2,946,652, German Laid-Open Application DOS No. 3,024,265, German Laid-Open Application DOS No. 3,004,770, European Pat. No. 2,800, European Pat. No. 3,114, European Pat. No. 23,785, European Pat. No. 24,932, European Pat. No. 29,319 and U.S. Pat. No. 4,236,912.

The Examples which follow illustrate the novel process.

EXAMPLE 1

550 g (5 moles) of hydroquinone in 2 liters of anhydrous dimethylsulfoxide were initially taken, and 185 g (2.5 moles) of calcium hydroxide were added. The mixture was stirred for 30 minutes after which it was cooled to 10° C. and 362 g (2 moles) of ethyl 2-bromopropionate were added dropwise in the course of 5 hours. After the addition was complete, the mixture was warmed to room temperature, stirred for a further 20 hours and then stirred into a mixture of 4 liters of ice water and 500 ml of 38% strength hydrochloric acid. The mixture was extracted with 3 liters of methylene chloride, and the methylene chloride solution was washed once with water.

345 g (1.643 moles) of ethyl 2-(4-hydroxyphenoxy)-propionate of the formula

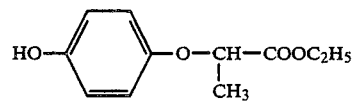

were obtained. Yield 82.3%; bp.=133°-136° C./0.2 mbar.

Analysis: $C_{11}H_{14}O_4$/M =210 Calculated: C 62.85% H 6.66% Found: C 62.6% H 6.5%

EXAMPLE 2

264 g (2.4 moles) of hydroquinone were dissolved in 800 ml of anhydrous dimethylsulfoxide, and 89 g (1.2 moles) of calcium hydroxide were added. The mixture was stirred for 30 minutes at room temperature, after which it was cooled to 10° C. 268 g (1.2 moles) of n-pentyl 2-bromopropionate were added dropwise in the course of 3 hours, while maintaining this temperature. Thereafter, the mixture was left to warm up to room temperature, and stirred for 20 hours at this temperature. Finally, the mixture was worked up as described in Example 1. 214 g (0.85 mole) of n-pentyl 2-(4-hydroxyphenoxy)-propionate were obtained. Yield: 70.8%; bp.=149°-150° C./0.2 mbar.

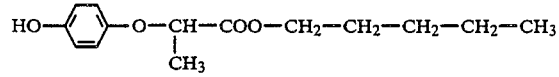

Analysis: $C_{14}H_{20}O_4$/M=252 Calculated: C 66.65% H 7.99% Found: C 65.9% H 7.9%

EXAMPLE 3

121 g (1.1 moles) of hydroquinone were dissolved in 500 ml of dimethylsulfoxide, 37 g (0.5 mole) of calcium hydroxide were added to the solution, and the mixture was stirred for 1 hour at 45°-50° C. Thereafter, 82.3 g (0.455 mole) of optically active n-butyl 2-chloropropionate ($\alpha_D^{20} = -13.0°$) were added dropwise in the course of 1 hour at the same temperature. The mixture was stirred for a further 3 hours at 45°-50° C., cooled, and worked up as described in Example 1. 49.7 g (0.21 mole) of optically active n-butyl 2-(4-hydroxyphenoxy)-propionate were obtained. Yield: 46.2%; bp. =150°-152° C./0.22 mbar; $\alpha_D^{20} = +11.8°$

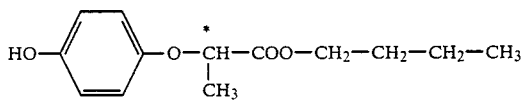 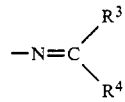

Analysis: $C_{13}H_{18}O_4/M=238$ Calculated: C 65.54% H 7.56% Found: C 65.3% H 7.5%

The reactions which are summarized in the Table below and which employ a 2-bromo-fatty acid ester as component III were carried out similarly to Example 1 (including the molar ratios given therein).

| Ex- | | Component III | | | Yield |
|---|---|---|---|---|---|
| ample | Component II | $R^1$ | $R^2$ | bp. (°C.) | % |
| 4 | hydroquinone | H | $C_2H_5$ | 140–144 (0.2 mbar) | 48.3 |
| 5 | " | $CH_3$ | $CH_3$ | 127–128 (0.2 mbar) | 79.4 |
| 6 | " | $CH_3$ | n-$C_3H_7$ | 139–142 (0.35 mbar) | 73.1 |
| 7 | " | $CH_3$ | n-$C_4H_9$ | 146–149 (0.2 mbar) | 76.1 |
| 8 | " | $C_2H_5$ | $C_2H_5$ | 138–142 (0.5 mbar) | 68.8 |
| 9 | resorcinol | $CH_3$ | $CH_3$ | 132 (0.2 mbar) | 65.7 |
| 10 | hydroquinone | $CH_3$ | n-$C_8H_{17}$ | 166–170 (0.25 mbar) | 58 |
| 11 | " | $CH_3$ | —$CH_2$—$CH=CH_2$ | 136–140 (0.15 mbar) | 62.2 |
| 12 | " | $CH_3$ | —$CH_2$—$C\equiv CH$ | 148–150 (0.2 mbar) | 65.5 |
| 13 | " | $CH_3$ | —N=C—$CH_3$ $CN_3$ | | |

$^1$H-NMR data for Example 13 (D$_6$DMSO; internal standard TMS chemical shift in δ-values [ppm]):

1.83 (s; —N=C(CH$_3$)—CH$_3$), 1.90 (s; —N=C(CH$_3$)—CH$_3$), 1.50 (d; $R^1$ = CH$_3$), 4.88 (q; —CH—).

Abbreviations: D$_6$DMSO = OS(CD$_3$)$_2$

TMS = tetramethylsilane

We claim:

1. A process for the preparation of a 2-(hydroxyphenoxy)-carboxylate of the formula:

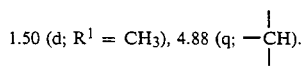

where $R^1$ is hydrogen or a low molecular weight alkyl group, and $R^2$ is a saturated or unsaturated hydrocarbon radical of no more than 10 carbon atoms which is unsubstituted or substituted by diphenoxy, cyano, halogen or trialkylsilyl, or is a radical of the formula:

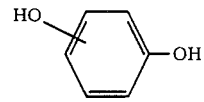

where $R^3$ and $R^4$ are each identical or different hydrocarbon radicals which are no more than 9 carbon atoms together or $R^3$ and $R^4$ are bonded to one another, which comprises reacting a compound of the formula:

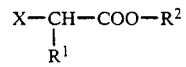

with a 2-halo-fatty acid ester of the formula:

$$X-CH(R^1)-COO-R^2$$

where $R^1$ and $R^2$ have the above meanings and X is chlorine or bromine, in the presence of calcium hydroxide as the base, in dimethylsulfoxide, at from 0° to +100° C., the molar ratio of the starting material II:III at the beginning of the reaction being not less than 1.5:1.

2. The process as claimed in claim 1, wherein, in the starting material III employed, $R^1$ is hydrogen, methyl or ethyl.

3. The process as claimed in claim 1, wherein the starting material III employed is optically active and its radical $R^1$ is alkyl.

4. The process as claimed in claim 1, wherein the starting material III is selected from the group consisting of methyl bromoacetate, ethyl chloroacetate, the methyl, ethyl, and -propyl, 2-phenoxyethyl, 3-phenoxypropyl, n-butyl, isobutyl, t-butyl, n-pentyl, n-octyl, 2-ethylhexyl, n-decyl, allyl, propargyl, 2-cyanoethyl, 1-cyanopropyl, 3-chloroallyl, 2, 3-dichloroallyl, 2-bromoallyl and phenyl esters of 2-chloro- and 2-bromopropionic acid, ethyl-2-bromobutyrate, 1-cyanocyclohexyl-2-bromobutyrate ethyl-2-bromovalerate, methyl-2-bromocaproate, 2-bromopropionylacetoxime and bromoacetylcyclohexanone oxime.

5. The process as claimed in claim 1, wherein 0.4 to 1.0 moles of calcium hydroxide or used per mole of the compound of formula II.

6. The process as claimed in claim 1, wherein said reaction is effected at a temperature in the range of 0° to +60° C.

* * * * *